United States Patent [19]
Pietzsch et al.

[11] 3,974,084
[45] Aug. 10, 1976

[54] PROCESS FOR THE MANUFACTURE OF ANHYDROUS ALKALI METAL ARYLATE SOLUTIONS AND SEPARATION OF THE ARYLATES FROM ALKALI METAL SULFITE

[75] Inventors: Siegfried Pietzsch, Kelkheim, Taunus; Georg Schaeffer, Hofheim, Taunus, both of Germany

[73] Assignee: Hoechst Aktiengesellschaft, Frankfurt am Main, Germany

[22] Filed: July 9, 1973

[21] Appl. No.: 377,231

[30] Foreign Application Priority Data
July 11, 1972  Germany............................ 2233940

[52] U.S. Cl. ............................ 252/182; 260/621 P; 260/627 C
[51] Int. Cl.² ................. C07C 39/00; C07C 37/22; C07C 37/24
[58] Field of Search ................ 252/182; 260/621 P, 260/627 C

[56] References Cited
UNITED STATES PATENTS

| | | | |
|---|---|---|---|
| 2,016,848 | 10/1935 | Akimoff | 260/621 P X |
| 2,152,851 | 4/1939 | Lecher et al. | 260/621 P |
| 2,193,336 | 3/1940 | Lecher et al. | 260/621 P |
| 2,745,882 | 5/1956 | Hale | 260/621 P |
| 2,807,643 | 9/1957 | Hartley | 260/621 P X |
| 2,858,342 | 10/1958 | Bender et al. | 260/621 P X |
| 2,968,679 | 1/1961 | Aelony | 260/621 P X |
| 3,056,842 | 10/1962 | Villars | 260/621 P X |

*Primary Examiner*—Herbert B. Guynn
*Attorney, Agent, or Firm*—Curtis, Morris & Safford

[57] ABSTRACT

Anhydrous organic solutions of alkali metal arylates are prepared by dissolving an alkali metal arylate or reacting an arylhydroxy compound with alkali metal hydroxide in a ketone immiscible or incompletely miscible with water at room temperature and removing the water from the solution, if any, by azeotropic distillation with reflux.

7 Claims, No Drawings

PROCESS FOR THE MANUFACTURE OF ANHYDROUS ALKALI METAL ARYLATE SOLUTIONS AND SEPARATION OF THE ARYLATES FROM ALKALI METAL SULFITE

This invention relates to a process for the manufacture of anhydrous alkali metal arylate solutions and to the separation of the arylates from alkali metal sulfite.

It is known that alkali metal arylates are soluble in organic solvents, for example alcohols, pyridines, and cyclic ethers (cf. Annales de Chimie (6), 30 (1893), page 60; Berichte der Deutschen Chemischen Gesellschaft 39 (1906), page 15; U.S. Pat. Nos. 2,152,851 and 2,193,336).

The alkali metal arylate solutions can be prepared by dissolving the respective arylate in the solvent or by reacting the corresponding arylhydroxy compound dissolved in the solvent with an alkali metal hydroxide.

These known processes have quite a number of disadvantages and do not permit or permit with high industrial expenditure only the manufacture of anhydrous solutions. Cyclic ethers tend to form peroxides to a higher extent than the commonly used aliphatic diethyl or diisopropyl ethers, so that severe safety precautions are necessary. 1,4-Dioxane, which is of industrial importance, as well as many compounds of the aforesaid alcohols or pyridines can be mixed with water without any limit so that a complicated dehydration is indispensible if anhydrous alkali metal arylate solutions are required. The quantitative removal of water from the aforesaid alkali metal solutions is not possible by a simple method, for example azeotropic distillation. Furthermore, with cyclic ethers and pyridines the heterogeneous reaction of arylhydroxy compounds, for example naphthol, with the alkali metal hydroxide is slow as the resulting alkali metal naphtholate forms with the water a sparingly soluble hydrate, so that even the use of pulverized alkali metal hydroxide has been recommended, the handling of which undoubtedly involves additional difficulties in an industrial process. Moreover, the reaction has to be carried out in a cold solvent since at elevated temperature the alkali metal hydroxide forms a second liquid phase with the water present or generated in the reaction, i.e., it separates from its reaction components, so that the reaction speed is further reduced. Finally, the cyclic ethers as solvents are only suitable for polynuclear alkali metal arylates.

With pyridines as solvent or reactant the conditions are similar to those required for the reaction of the aryl hydroxy compounds with alkali metal hydroxides. Moreover, the solubility of some alkali metal arylates or their hydrates is not satisfactory. As low molecular weight pyridines are also miscible with water to any extent, the azeotropic dehydration of the alkali metal arylate solution should either be started with a cumbersome excess of pyridine or the amount of pyridine distilled off should be replenished continuously with dehydrated pyridine. Owing to the solubility in water of the pyridines, the usual recycling of the entrainer is not possible.

The conditions are alike with low molecular weight aliphatic alcohols, whereas alcohols having a higher molecular weight can be freed from water by azeotropic distillation. But the use of alcohols is little expedient as in the alkaline medium their reactive hydroxyl groups may have properties similar to those of the arylhydroxy compounds and thus may disturb the further processing of the aromatic compounds. Hence, an industrial use of such anhydrous alcoholic alkali metal arylate solutions for the manufacture of, for example, aryl-chloroformates and diaryl carbonates, is practically impossible.

It has also been proposed to separate into their sulfite and arylate components so-called "alkali melts" obtained in industry, for example in the manufacture of naphthols, by reacting sodium naphthalene sulfonate with caustic soda and containing sodium naphtholate and sodium sulfite. The pulverized alkali melts are treated with a pyridine or a cyclic ether at elevated temperature whereby the sodium naphtholate passes into solution while the sodium sulfite remains undissolved together with the caustic soda in excess. To isolate the naphthol water is added to the filtered sodium naphtholate solution, the difficulty soluble hydrate of sodium naphtholate, which precipitates in the pyridine or the cyclic ether, is separated and, after redissolution in water, the arylhydroxy compound is set free by adding an acid. In principle, this process is rather complicated and uneconomical as the entire amount of alkali metal hydroxide is not recovered and remains in the waste water as a salt. Moreover, working with pyridines and cyclic esters is not very pleasant and, especially in the case of pyridine, residues thereof cannot be eliminated completely without considerable expenditure. The residues of pyridine or cyclic ether adhering to the sodium sulfite and/or the hydrate of the naphtholate, which either disturb the further processing of the sulfite or come into the waste water via the aqueous solution of the naphtholate, constitute in any case a pollution problem.

The present invention provides a process for the manufacture of anhydrous alkali metal arylate solutions which comprises dissolving an alkali metal arylate which may contain water or reacting an arylhydroxy compound with an alkali metal hydroxide in a ketone as a solvent and removing the water from the solution by axeotropic distillation, the separating ketone acting as an entrainer possibly being recycled into the boiling solution in usual manner. As compared with the known process, the use of a ketone as a solvent has the advantage that the alkali metal arylates and the hydrates thereof dissolve more rapidly and easily so that the dissolution of the solid matter is facilitated and the formation of a difficultly soluble alkali metal arylate hydrate precipitate is avoided. Moreover, ketones as solvents are much better to handle in industry. The ketones constitute relatively inert solvents for alkaline solutions which allow for removing by simple azeotropic distillation the water contained in the solutions or formed by chemical reaction (neutralization). Hence, anhydrous ketonic alkali metal arylate solutions are obtained in simple manner from water-containing alkali metal arylate solutions, which ketonic solutions can be used for further reactions in which the absence of water is favourable or required. A reaction of this type is that of an alkali metal arylate with phosgene in which aryl-chloroformates or diaryl carbonates are formed. The technical advantage of such a reaction is that it takes place in homogeneous phase in the absence of water, whereby an excessive consumption of phosgene is avoided. The aryl-chloroformates produced in this manner are starting compounds for producing many plant protecting agents.

The alkali metal arylate, which may be in a pure state or admixed with by-products, such as caustic soda or sulfite, is dissolved in the ketone simply by heating. When the ketonic solution is prepared by reacting an arylhydroxy compound with an alkali metal hydroxide, the latter is added to the solution of the arylhydroxy compound in the ketone. The alkali metal hydroxide can be added in pieces; it need not be pulverized. Reaction and dissolution are completed by heating and simultaneously the water formed is separated by azeotropic distillation.

It has also been found that the sulfite contained in "alkali metals" (alkali metal arylate melts), for example originating from the naphthol fabrication, can be separated in solid form practically quantitatively from the alkali metal arylate and the excess alkali metal hydroxide by treating the solid product from the melt with a ketone as a solvent or pouring the liquid melt into the ketone. In the former case, the alkali metal arylate and the caustic soda in excess are dissolved out of the solidified melt and separated from the insoluble alkali metal sulfite. It is not necessary to pulverize the melt or comminute it to small pieces. Even big lumps of several kilograms can be dissolved rapidly and easily by boiling in the ketone, optionally in the presence of small amounts of water up to about 2% by weight, calculated on the amount of solvent used. Subsequently, the water may be removed from the ketonic arylate solution by azeotropic distillation. In the latter case, the liquid melt, for example from the naphthol fabrication, is run into the ketone, while the heat introduced into the ketone by the melt is dissipated either by external cooling or by a boiling reflux. When the liquid melt is introduced into the ketone, the alkali metal arylate and the excess alkali metal hydroxide are dissolved while the alkali metal sulfite separates in the form of crystals.

Independent of the method of separation of the alkali metal sulfite, the process of the invention is rapid and simple and can be carried out without difficulties. The undissolved sulfite is separated by suction filtration or centrifugation.

The dissolution of the alkali arylate and alkali metal hydroxide in excess from the alkali melt and the separation of the sulfite, as well as the preparation of the alkali metal arylate solutions by physical dissolution or chemical reaction (neutralization) can be carried out at a temperature as low as 15°C when care is taken that the solvent is sufficiently kept in motion by a stirrer. In general, the processes are performed at a temperature in the range of from 15° to 200°C, preferably 50° to 150°C, more preferably the boiling temperature of the ketone used or of its azeotrope with water if the latter is present.

Suitable solvents and reaction medium in the process of the invention are all liquid and solid ketone compounds having a boiling point above 75°C and a melting point below 120°C, preferably not exceeding 100°C. They sould be immiscible or sparingly miscible with water. Solid ketones may be used in the manufacture of the alkali metal arylates or their isolation from the alkali melts and their further reaction (for example as starting material for chemical reactions) can be carried out at temperatures of up to 200°C, or a subsequent hydrolysis to obtain the free arylhydroxy compound, as described below, can be carried out at temperatures of up to 150°C, optionally under pressure.

As already mentioned, the ketones used in the process of the invention should be immiscible or sparingly miscible with water. The ketone should dissolve at most 15% by weight of water at 25°C, are preferably less than 5%. Such ketones are, for example, carbonyl compounds having straight chain or branched alkyl radicals, phenyl radicals or cycloaliphatic radicals. Suitable ketones are, for example, araliphatic ketones such as acetophenone; aromatic ketones such as benzophenone; cyclic ketones, such as cycloheptanone or isophorone; more preferably, however, aliphatic ketones with saturated or unsaturated alkyl radicals; the ketones may have up to 17 carbon atoms. Especially preferred are linear and branched aliphatic ketones with 4 to 12 carbon atoms, such as, for example, diethyl ketone, methylisobutyl ketone, di-n-propyl ketone, diisopropyl ketone, ethyl-n-butyl ketone, methyl tert-.butyl ketone, dissobutyl ketone and decan-2-one.

In the process of the invention practically all monohydroxyaryl compounds not containing additional ionic or ionogenic groups are suitable. Examples of such compounds are especially α- and β- naphthols, their alkyl compounds, preferably methyl and ethyl compounds, chloronaphthols, as mononuclear compounds phenol, methyl and ethyl phenols, mono- and polysubstituted chlorophenols and phenol compounds which contain an additional bound aromatic nucleus. Unsuitable are especially those phenolic compounds which contain a further phenolic hydroxy group or sulfonic acid group or another water-solubilizing group. Especially good results are obtained with alkyl melts of α- and β-naphthols.

The anhydrous alkali metal arylate solutions obtained according to the invention can be directly used for further reactions. When the alkali metal arylate solutions have not been prepared by neutralization of the corresponding arylhydroxy compounds with alkali metal hydroxide they can be separated into their components, i.e., arylhydroxy compound and alkali metal hydroxide by aqueous hydrolysis. In this process water is added to the ketonic solution and the alkali metal hydroxide is separated therefrom. The alkali metal arylate solution obtained can be separated exhaustively into a ketonic phase containing the dissolved pure arylhydroxy compound and an aqueous alkali metal hydroxide solution. A prerequisite for the separation of these compounds is a sufficient hydrolysis of the alkali metal arylate in aqueous solution and a favorable distribution of the arylhydroxy compound between the organic phase and the aqueous alkali metal arylate or alkali metal hydroxide solution. In this simple manner, it is possible not only to separate practically quantitatively the sulfite free from caustic alkali from an alkali melt, but also to work up quantitatively the arylhydroxy compound in the form of its alkali metal salt and the excess of caustic alkali, and to isolate practically quantitatively a pure arylhydroxy compound and alkali metal hydroxide solution which may be reused, for example in the naphthol melting process. In the case of sodium naphtholate the entire amount of naphthol is thus obtained in ketonic solution and can be isolated, for example by distillation of the solvent and subsequent distillative purification.

The alkali metal hydroxide solution obtained in this process is free from sulfite as the sulfite had already been separated prior to the hydrolytic extraction. It can be reused in the melting process which means optimum utilization.

As compared with pyridines and cyclic ethers, the ketones to be used in the process of the invention have advantages not only as solvents for the alkali metal arylates but also as reaction medium in their preparation. Owing to the fact that the alkali metal arylates are free from water and are soluble in the ketones even in the form of their hydrates, the alkali metal hydroxide used for the reaction with the aryl hydroxy compound need not be pulverized but can be used in the form of coarse grains. Contrary to the state of the art, the production of the alkali metal arylates is not limited to room temperature; it is likewise possible to effect the reaction in boiling ketone which reduces the reaction period. The reaction water formed can be distilled off azeotropically and, owing to its insolubility in water, the ketone can be recycled as entrainer. Without doubt, this is a particular advantage over the known use of pyridines and cyclic ethers which are soluble in water. The elimination of the reaction water according to the state of the art with an excess of alkali metal hydroxide by separating into an organic and an aqueous phase or with conventional drying agents as used with cyclic ethers can be dispensed with.

Owing to the fact that the ketones used in the present process are immiscible or miscible to a small extent only with water and, hence, with aqueous alkali metal hydroxide solutions, and that the individual components are quantitatively separated and thus do not cause sewage problems, a true industrial progress is achieved. The separation of the alkali metal arylate from the sulfite means that no acids are necessary, that the alkali metal hydroxide used is recovered and that no waste water is formed.

According to the state of the art the known separation of alkali melts into alkali metal arylates and alkali metal sulfite can also be carried out with high molecular weight water-in-soluble or limitedly water-soluble alcohols, pyridines and cyclic ethers. It is not possible, however, to separate the alkali metal arylate solutions obtained into their components without using the commonly used process of working up the aqueous solution or separating the alkali metal arylate in the form of its hydrate, dissolving the hydrate in water and neutralizing or acidifying the solution and isolating the arylhydroxy compound set free, possibly by extraction with a usual organic solvent. As compared therewith, the isolation of arylhydroxy compounds and separation of alkali metal hydroxide, which can be used in combination with the present process of separating the alkali metal arylate from the sulfite by means of a ketone as solvent, requires much less expenditure. If in the present process the specified alcohols, pyridines or cyclic ethers were used to decompose the alkali melt in accordance with the invention, a combination with the aforesaid isolating process is not possible due to the unsatisfactory distribution of the arylhydroxy compound and the alkali metal hydroxide between the organic and the aqueous phase.

The following examples illustrate the invention.

EXAMPLE 1

A solution of 9.4 g of phenol in 100 g of methylisobutyl ketone was boiled with 4.0 a of solid sodium hydroxide using a conventional water separator. The water contained in the ketonic solution was separated by azeotropic distillation while the ketone, separating from the water in the distillate, was continuously recycled into the ketonic phenolate solution. The boiling temperature was 117°C. After 1.5 hours, 1.8 g of water had separated. In the ketonic solution the sodium phenolate obtained remained dissolved at room temperature.

EXAMPLE 2

A solution of 1.29 kilograms of o-chlorophenol in 10 kg of di-isopropyl ketone was boiled, using a water separator, with 400 g of solid sodium hydroxide. After azeotropic distillation for 1 hour at 127°C, 180 g of water had separated.

The sodium salt of o-chlorophenol obtained remained dissolved in the anhydrous ketone at room temperature.

EXAMPLE 3

An anhydrous salt solution was obtained by reacting in analogous manner 170 g of 2-hydroxy-diphenyl in 1000 g of methylisobutyl ketone with 40 g of sodium hydroxide.

EXAMPLE 4

A solution of 14.4 g of $\alpha$-naphthol in 100 g of diisobutyl ketone was refluxed azeotropically for 1 hour at 172°C with 4.0 g of sodium hydroxide and simultaneously the water contained in the ketonic solution was quantitatively separated by a water separator. An anhydrous ketonic sodium-$\alpha$-naphtholate solution was obtained in which the salt remained dissolved at room temperature.

A anhydrous sodium-$\beta$-naphtholate solution was obtained in analogous manner by using as solvent diisopropyl ketone or methylisobutyl ketone.

EXAMPLE 5

A solution of 179 g of 1-chloronaphthol-2 in 1,000 g of methylisobutyl ketone was refluxed with 40 g of sodium hydroxide using a water separator. After 80 minutes at a boiling temperature of 117°C the water was completely separated by azeotropic distillation. The naphtholate in the anhydrous solution remained dissolved at room temperature.

EXAMPLE 6

In a manner analogous to that described in the preceding examples an anhydrous ketonic solution of the disodium salt of bis(2-hydroxy-1-naphthyl)methane in methylisobutyl ketone was obtained by refluxing for 2 hours at 117°C 15.0 g of the hydroxy compound in 100 g of the ketone with 4.0 g of sodium hydroxide.

EXAMPLE 7

245 Grams of an alkali melt originating from the naphthol production and containing 130 g of sodium-$\beta$-naphtholate and 99 g of sodium sulfite were boiled (reflux temperature 117°C) in the form of solid lumps with 1,600 g of methylisobutyl ketone. In the course of 30 minutes the lumps of the melt decomposed completely, the sodium naphtholate dissolved and the sodium sulfite separated in the form of coarse crystals. The hot solution was filtered off with suction from the deposit which corresponded to the theoretical amount of sodium sulfite. The ketonic solution contained the corresponding amount of sodium-$\beta$-naphtholate and the residual sodium hydroxide.

The isolate the arylhydroxy compound the $\beta$-naphtholate solution was refluxed at an azeotropic boiling temperature of 87°C for 30 minutes while thoroughly stirring, the hot ketone phase was separated and shaken once with 250 ml of water. After distillation of the solvent, 47 g of β-naphthol melting at 114°–118°C were obtained.

The aqueous phase containing the rest of the β-naphthol and the entire amount of alkali was extracted continuously for 5 hours at the boil with methylisobutyl ketone. The remaining portion of 66 g of β-naphthol was thus isolated. The naphthol melted at 118°–120°C. The aqueous phase remaining behind was pure sodium hydroxide solution containing the equivalent amount of NaOH.

EXAMPLE 8

210 Grams of solid lumps of an alkali melt originating from the α-naphthol production and containing 110 g of sodium-α-naphtholate and 84 g of sodium sulfite were boiled with 1,350 g of methylisobutyl ketone. At a boiling temperature of 117°C the lumps decomposed completely. The crystalline sodium sulfite was filtered off with suction from the hot solution; the amount corresponded to the theory. The filtrate contained the dissolved sodium-α-naphtholate and the residual sodium hydroxide.

For complete isolation of the α-naphthol and recovery of the alkali metal hydroxide the ketonic solution was refluxed for 30 minutes at an azeotropic boiling temperature of 87°C while thoroughly stirring with 1,350 g of water. The hot ketone phase was separated and shaken once with 210 ml of water. After distillation of the solvent, 31 g of α-naphthol melting at 86°–91°C were isolated from the ketone phase. The aqueous phase which contained the rest of the α-naphthol and the total amount of alkali was continuously extracted for 6 hours at an azeotropic boiling temperature of 87°C with methylisobutyl ketone, and from the separated organic phase the residual 64 g of α-naphthol melting at 90°–93°C were obtained. The aqueous phase consisted of sodium hydroxide solution whose content of NaOH was equivalent to that of the alkali melt used.

What is claimed is:

1. A process for the manufacture of an anhydrous ketonic solution of an alkali metal arylate free from alkali metal sulfite which comprises, at a temperature in the range of about 15° to about 200°C.: dissolving (A) a melt product containing (1) an alkali metal arylate wherein said arylate is phenolate, naphtholate, phenolate substituted on the aromatic nucleus by at least one methyl, ethyl, phenyl or chlorine, naphtholate substituted on the aromatic nucleus by at least one methyl, ethyl, phenyl or chlorine, or mixtures thereof, (2) an alkali metal hydroxide and (3) an alkali metal sulfite in (B) a ketone that is immiscible with water or that is miscible with at most about 15% of water at room temperature, said ketone having up to 17 carbon atoms and being an araliphatic ketone, an aromatic ketone, a cyclic ketone, an aliphatic ketone, or a mixture thereof; removing undissolved alkali metal sulfite from the ketonic solution; and thereafter removing any water from the ketonic solution by azeotropic distillation thereof.

2. A process according to claim 1 wherein said process is conducted at temperatures in the range of about 50° to about 150°C.

3. A process according to claim 1 wherein said ketone has a boiling point above about 75°C. and a melting point below about 120°C.

4. A process according to claim 1 wherein said ketone is miscible with less than about 5% by weight of water at 25°C.

5. A process according to claim 1 wherein said alkali metal is sodium or potassium.

6. A process according to claim 1 wherein said ketone has 4 to 12 carbon atoms and is a linear or branched aliphatic ketone.

7. A process according to claim 1 wherein said ketone is diethyl-ketone, methylisobutyl-ketone, di-n-propyl-ketone, diisopropyl-ketone, ethyl-n-butyl-ketone, methyl-tert.butyl-ketone, diisobutyl-ketone, decanone-2, acetophenone, benzophenone, cycloheptanone, isophorone or a mixture thereof.

* * * * *